United States Patent [19]

Koch et al.

[11] Patent Number: 4,954,529
[45] Date of Patent: Sep. 4, 1990

[54] (THIO)BENZOYLUREAS AND FUNCTIONAL DERIVATIVES THEREOF, PROCESSES FOR THEIR PREPARATION, AGENTS CONTAINING THEM AND THEIR USE AS AGENTS FOR COMBATING PESTS

[75] Inventors: Volker Koch, Kelkheim; Stefan Schnatterer, Frankfurt am Main; Werner Bonin, Kelkheim; Manfred Kern, Lörzweiler; Werner Knauf, Eppstein/Taunus; Anna Waltersdorfer, Frankfurt am Main, all of Fed. Rep. of Germany

[73] Assignee: Hoechst Aktiengesellschaft, Frankfurt am Main, Fed. Rep. of Germany

[21] Appl. No.: 278,966

[22] Filed: Dec. 2, 1988

[30] Foreign Application Priority Data

Dec. 4, 1987 [DE] Fed. Rep. of Germany ....... 3741062

[51] Int. Cl.$^5$ .................... A01N 47/30; C07C 275/02; C07C 275/54
[52] U.S. Cl. ..................................... 514/594; 544/67; 564/23; 564/44; 514/229.2; 514/584
[58] Field of Search ............................ 564/44; 514/594

[56] References Cited

U.S. PATENT DOCUMENTS

| 4,005,223 | 1/1977 | Sirrenberg et al. | 424/322 |
| 4,150,158 | 4/1979 | Huff | 424/248.57 |
| 4,200,653 | 4/1980 | Huff et al. | 424/322 |
| 4,459,297 | 7/1984 | Lange et al. | 424/248.58 |

FOREIGN PATENT DOCUMENTS

| 921470 | 2/1973 | Canada. | |
| 1234819 | 4/1988 | Canada. | |
| 0084652 | 8/1983 | European Pat. Off. | |
| 0136745 | 4/1985 | European Pat. Off. | 514/594 |
| 0156765 | 6/1988 | Japan | 564/44 |
| 0285428 | 10/1988 | Japan | 564/44 |

Primary Examiner—Glennon H. Hollrah
Assistant Examiner—Susan P. Treanor
Attorney, Agent, or Firm—Curtis, Morris & Safford

[57] ABSTRACT

Compounds of the general formula I

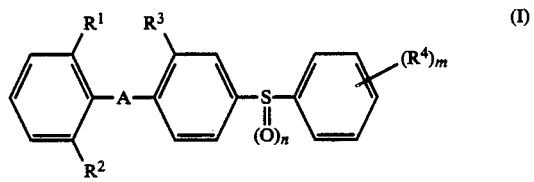

in which A denotes a radical of the formula $A^1$, $A^2$ or $A^3$

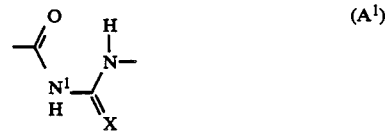

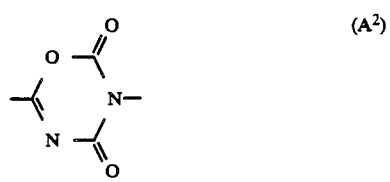

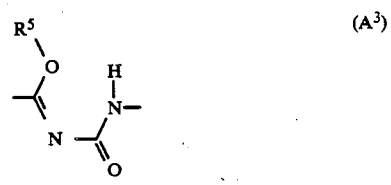

$R^1$ to $R^3$ in each case independently of one another denote hydrogen or halogen,
the radicals $R^4$ in each case independently of one another denote halogen, ($C_1$–$C_3$)halogenoalkyl or nitro,
$R^5$ denotes ($C_1$–$C_5$)alkyl, which can be halogenated,
X denotes oxygen or sulfur,
n denotes a number from 0 to 2 and
m denotes a number from 1 to 4 with the proviso that $(R^4)_m$ does not by itself denote halogen or by itself denote nitro, and where $A=A^1$, salts thereof which can be used in agriculture, have advantageous acaricidal and insecticidal properties.

Processes for the preparation of the compounds of the formula I are furthermore described.

11 Claims, No Drawings

(THIO)BENZOYLUREAS AND FUNCTIONAL DERIVATIVES THEREOF, PROCESSES FOR THEIR PREPARATION, AGENTS CONTAINING THEM AND THEIR USE AS AGENTS FOR COMBATING PESTS

DESCRIPTION

It is known that certain (thio)benzoylureas and functional derivatives thereof have insecticidal and acaricidal properties, see DE-OS No. 2,537,413, EP-A No. 84,652 and EP-A No. 5,944.

However, in some cases these have inadequate activities.

Novel substituted (thio)benzoylureas and functional derivatives derived from these having advantageous properties for combating pests have been found.

The present invention thus relates to the compounds of the formula I

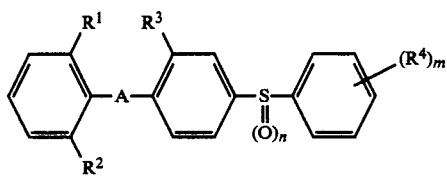

in which A denotes a radical of the formula $A^1$, $A^2$ or $A^3$

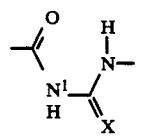

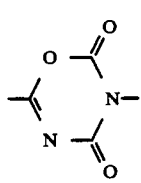

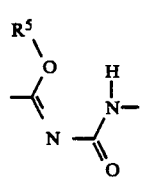

$R^1$ to $R^3$ in each case independently of one another denote hydrogen or halogen, the radicals $R^4$ in each case independently of one another denote halogen, $(C_1-C_3)$halogenoalkyl or nitro, $R^5$ denotes $(C_1-C_5)$alkyl, which can be halogenated, x denotes oxygen or sulfur, n denotes a number from 0 to 2 and m denotes a number from 1 to 4 with the proviso that $(R^4)_m$ does not exclusively denote halogen or does not exclusively denote nitro, and where $A=A^1$, salts thereof which can be used in agriculture.

Halogen denotes F, Cl, Br or I, in particular F or Cl. Halogenated and halo are likewise to be understood as the abovementioned substituents. Halogenoalkyl denotes, in particular, $CF_3$.

Preferred compounds of the formula I are those in which $R^1$ denotes Cl or F and $R^2$ denotes H or F; $R^3$ denotes H or F and the radicals $R^4$ in each case independently of one another denote Cl, F, $CF_3$ or nitro; $R^5$ denotes ethyl; X denotes oxygen; n denotes 0 and m denotes 1 to 3, and where $A=A^1$, salts thereof which can be used in agriculture.

Particularly preferred compounds of the formula I are those in which $R^1$ denotes Cl or F and $R^2$ denotes H or F; $R^3$ denotes H or F and $(R^4)_m$ denotes 2-Cl or 4-$CF_3$; $R^5$ denotes ethyl; X denotes oxygen; n denotes 0 and m denotes 1 or 2, and where $A=A^1$, salts thereof which can be used in agriculture.

Of the two groups last mentioned, compounds of particular importance are those in which A denotes a radical of the formula $A^1$ or $A^3$. The following compounds may be mentioned in particular here:

N-(2-chlorobenzoyl)-N'-(4-(2-chloro-4-trifluoromethyl-1-phenylmercapto)phenyl)urea, N-(2-fluorobenzoyl)-N'-(4-(2-chloro-4-trifluoromethyl-1-phenylmercapto)phenyl)urea, N-(2,6-difluorobenzoyl)-N'-(4-(2-chloro-4-trifluoromethyl-1-phenylmercapto)phenyl)urea, N-(2-chlorobenzoyl)-N'-(4-(2-chloro-4-trifluoromethyl-1-phenylmercapto)-2-fluorophenyl)urea, N-(2-fluorobenzoyl)-N'-(4-(2-chloro-4-trifluoromethyl-1-phenylmercapto)-2-fluorophenyl)urea, N-(2,6-difluorobenzoyl)-N'-(4-(2-chloro-4-trifluoromethyl-1-phenylmercapto)-2-fluorophenyl)urea, ethyl N-(N-(2-chloro-4-trifluoromethyl-1-phenylmercapto)phenyl)carbamoyl)-2-chlorobenzocarboximidate, ethyl N-(N-(2-chloro-4-trifluoromethyl-1-phenylmercapto)phenyl)carbamoyl)-2-fluorobenzocarboximidate and ethyl N-(N-(2-chloro-4-trifluoromethyl-1-phenylmercapto)phenyl)carbamoyl)-2,6-difluorobenzocarboximidate.

The invention also includes all the stereoisomers, and mixtures thereof, of the compounds of the formula I, such as the E- and Z-isomers in the case of unsaturated structures or optical isomers if chirality centers occur. The compounds of the formula I can furthermore be in tautomeric forms, depending on the substitution, and the invention likewise includes these.

The invention also includes salts of the compounds of the formula I, where $A=A^1$, which can be formed by deprotonation on the $N^1$ atom.

Possible salts of the compounds of the formula I are the salts which can be used in agriculture, in particular the alkali metal, alkaline earth metal or ammonium salts or ammonium salts which are substituted by one to four organic radicals (such as alkyl or hydroxyalkyl).

The present invention also relates to processes for the preparation of the compounds of the formula I, which comprise (a) where $A=A^1$ ($a_1$) reacting a compound of the formula II

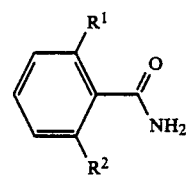

in which $R^1$ and $R^2$ have the meanings as in formula I, with a compound of the formula III

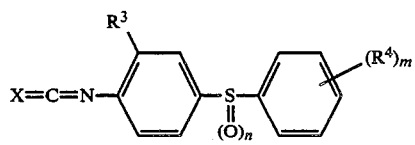

in which X, $R^3$, $R^4$, m and n have the meanings as in formula I, or ($a_2$) reacting a compound of the formula IV

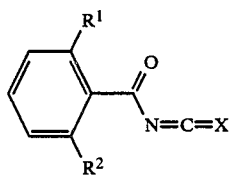

in which $R^1$, $R^2$ and X have the meanings as in formula I, with a compound of the formula V

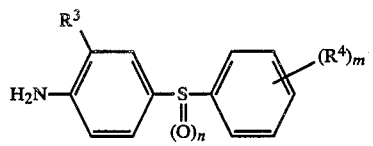

in which $R^3$, $R^4$, m and n have the meanings as in formula I, or (b) where $A=A^2$ reacting a compound of the formula III with a compound of the formula IV, in which X in each case denotes 0, or (c) where $A=A^3$ ($c_1$) reacting a compound of the formula VI

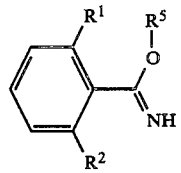

in which $R^1$, $R^2$ and $R^5$ have the meanings as in formula I, with a compound of the formula III, or ($c_2$) reacting a compound of the formula VII

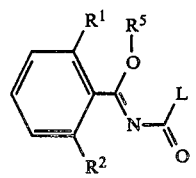

in which $R^1$, $R^2$ and $R^5$ have the meanings as in formula I and L stands for a nucleofugic leaving group, with a compound of the formula V.

Examples of the nucleofugic leaving group L which may be mentioned are:

halogen, ($C_1$–$C_3$)alkylthio, ($C_1$–$C_3$)haloalkoxy, triazolyl or imidazolyl.

The preparation of the benzamides II and benzoyliso(thio)cyanates IV is known from the literature (compare J. Agr. Food Chem. 21, 348 and 993 (1973); and Houben-Weyl E4, page 806 and page 869).

The iso(thio)cyanates III are obtained from the anilines of the formula V by methods which are known from the literature (Houben-Weyl E4, page 738 and page 834).

The anilines of the formula V can be prepared by processes analogous to those known from the literature, and in particular (a) by reaction of corresponding 4-mercaptoanilines with substituted halogenobenzenes (Houben-Weyl E 11/1, page 175)

(b) by reaction of optionally substituted nitrothiophenols with substituted halobenzenes (it being possible for these thiodiphenyl ethers then to be oxidized to sulfoxides and sulfones, see Houben-Weyl E 11/1, page 702 et seq. and E 11/2, page 1194 et seq.) and subsequent reduction of the nitro group (Houben-Weyl E 11/1, page 175 and 4/1c, page 506 et seq. and 742) and (c) by reaction of substituted thiophenols with halonitrobenzenes (it being possible for these thiodiphenyl ethers then to be oxidized to sulfoxides and sulfones (cf. b)) and subsequent reduction of the nitro group (cf. b)). The compounds of the formula V are novel in some cases and in this respect are likewise the subject matter of the present invention.

The imidates of the formula VI are known from the literature (DE-OS No. 3,514,450).

The compounds of the formula VII can be prepared from the imidates of the formula VI by methods which are known from the literature (EP-A No. 135,894).

The reaction conditions (for example solvents, reaction temperature and catalysts) for the preparation and isolation of the compounds of the formula I are known from the literature:

Process variant ($a_1$), ($a_2$) for example DE-A No. 2,123,236

(b) for example U.S. Pat. No. 4,150,158

($c_1$), ($c_2$) for example EP-A No. 135,894

The active compounds have a good plant tolerance and favorable toxicity to warm-blooded animals and are suitable for combating animal pests, in particular insects, arachnids, helminths and molluscs, and especially preferably for combating insects and arachnids, which occur in agriculture, in animal husbandry, in forests, in the preservation of stored products and materials and in the hygiene sector. They are active against normally sensitive and resistant species and against all or individual stages of development. The abovementioned pests include:

From the order of the Acarina, for example *Acarus siro*, Agras spp., Ornithrodoros spp., *Dermanyssus gallinae*, *Eriophyes ribis*, *Phyllocoptruta oleivora*, Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa*, Panonychus spp., Tetranychus spp., Eotetranychus spp., Oligonychus spp. and Eutetranychus spp.

From the order of the Isopoda, for example *Oniscus asselus*, *Armadium vulgare* and *Porcellio scaber*.

From the order of the Diplopoda, for example *Blaniulus guttulatus*.

From the order of the Chilopoda, for example *Geophilus carpophagus* and Scutigera spp.

From the order of the Symphyla, for example *Scutigerella immaculata*.

From the order of the Thysanura, for example *Lepisma saccharina*.

From the order of the Collembola, for example *Onychiurus armatus*.

From the order of the Orthoptera, for example *Blatta orientalis, Periplaneta americana, Leucophaea maderae, Blatella germanica, Acheta domesticus,* Gryllotalpa spp., *Locusta migratoria migratorioides, Melanoplus differentialis* and *Schistocerca gregarai*.

From the order of the Dermaptera, for example *Forficula auricularia*.

From the order of the Isoptera, for example Reticulitermes spp.

From the order of the Anoplura, for example *Phylloera vastatrix,* Pemphigus spp., *Pediculus humanus corporis,* Haematopinus spp. and Linognathus spp.

From the order of the Mallophaga, for example Trichodectes spp. and Damalinea spp.

From the order of the Thysanoptera, for example *Hercinothrips femoralis* and *Thrips tabaci*.

From the order of the Heteroptera, for example Eurygaster spp., *Dysdercus intermedius, Piesma quadrata, Cimex lectularius, Rhodnius prolixus* and Triatoma spp.

From the order of the Homoptera, for example *Aleurodes brassicae, Bemisia tabaci, Trialeurodes vaporarium, Aphis gossypii, Bravicornyne brassicae, Cryptomyzus ribis, Doralis fabae, Doralis pomi, Eriosoma lanigerum, Hyalopterus arundinis, Macrosiphium avenae,* Myzus spp., *Phorodon humuli, Rhopalosiphum padi,* Empoasca spp., *Euscelus bilobatus, Naphotettix cincticeps, Lecanium corni, Saissetia oleae, Laodelphax striatellus, Nilaparvata lugens, Aonidiella auroantii, Apidiotus hederae,* Pseudococcus spp. and Psylla spp.

From the order of the Lepidoptera, for example *Pectinophora gossypiella, Bupalus piniarius, Cheimatobia brumata, Lithocolletis blancardella, Hyponomeuta padella, Plutella maculipennis, Malacosma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., Trichoplusia ni, *Carpocapsa pomonella,* Pieris spp., Chilo spp., *Pyrausta nubilalis, Ephestia kuehniella, Galleria mellonella, Cocoecia podana, Capua reticulana, Choristoneura fumiferana, Clysia ambiguella, Homona magnanima* and *Tortrix viridana*.

From the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylloides chrysocephala, Epilachna varivestis,* Atomaria spp., *Oryzaephilus surinamensis,* Anthonumus spp., Sitophilus spp., *Oriotthynchus sulcatus, Cosmopolites sordidus, Ceuthorrhynchus assimilis, Hypera postica,* Dermestes spp., Trogoderma, Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon slstritialis* and *Costelytra zealandica*.

From the order of the Hymenoptera, for example Diprion spp., Hoplocampa spp., Lasius spp., *Monomorium pharaonis* and Vespa spp.

From the order of the Diptera, for example Aedes spp., Anopheles spp., Culex spp., *Drosophila melanogaster,* Musca spp., Fannia spp., *Calliophora erythrocephala,* Lucilia spp., Chrysomyia spp., Cuterebra spp., Gastrophilus spp., Hypobosca spp., Stomoxys spp., Oestrus spp. Hypoderma spp., Tabanus spp., Tannia spp., *Bibio hortulanus, Oscinella frit,* Phorbia spp., *Pegomyia hyoscyami, Ceratitis capitata, Dacus oleae* and *Tripula paludosa*.

From the order of the Siphonaptera, for example *Xenopsylla cheopsis* and Ceratophyllus spp.

From the order of the Arachnida, for example *Scorpio maurus* and *Latrodectus mactans*.

From the class of Helminths, for example Haemonchus, Trichostrongulus, Ostertagia, Cooperia, Chabertia, Strongyloides, Oesophagostomum, Hyostrongulus, Ancylostoma, Ascaris and Heterakis and also Fasciola, and phytotoxic nematodes, for example those of the genera Meloidogyne, Heterodera, Ditylenchus, Aphelenchoides, Radopholus, Globodera, Pratylenchus, Longidorus and Xiphinema.

From the class of Gastropoda, for example Deroceras spp., Arion spp., Lymnaea spp., Galba spp., Succinea spp., Biophalaria spp., Bulinus spp. and Oncomelania spp.

From the class of Bivalva, for example Dreissena spp.

The invention also relates to agents which contain the compounds of the formula I, in addition to suitable formulation auxiliaries.

The agents according to the invention in general contain the active compounds of the formula I in amounts of 1 to 95% by weight.

They can be formulated in various ways, depending on the biological and/or chemico-physical parameters. Suitable formulation possibilities are thus: wettable powders (WP), emulsifiable concentrates (EC), aqueous solutions (SC), emulsions, sprayable solutions, oil- or water-based dispersions (SC), suspoemulsions (SC), dusting agents (DP), dressing agents, granules in the form of microgranules, spraying granules, coated granules and adsorption granules, water-dispersible granules (WG), ULV formulations, microcapsules, waxes or baits.

These individual types of formulation are known in principle and are described, for example, in: Winnacker-Küchler, "Chemische Technologie (Chemical Technology)", Volume 7, C. Hauser Verlag Munchen, 4th edition 1986; van Falkenberg, "Pesticides Formulations", Marcel Dekker N.Y., 2nd edition 1972–73; and K. Martens, "Spray Drying Handbook", 3rd edition 1979, G. Goodwin Ltd. London.

The formulation auxiliaries required, such as inert materials, surfactants, solvents and other additives, are likewise known and are described, for example, in: Watkins, "Handbook of Insecticide Dust Diluents and Carriers", 2nd edition, Darland Books, Caldwell N.J.; H. v. Olphen, "Introduction to Clay Colloid Chemistry", 2nd edition, J. Wiley & Sons, N.Y.; Marschen, "Solvents Guide", 2nd edition, Interscience, N.Y. 1950; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte (Surfaceactive ethylene oxide adducts)", Wiss. Verlagsgesell., Stuttgart 1976; Winnacker-Küchler, "Chemische Technologie (Chemical Technology)", Volume 7, C. Hauser Verlag München, 4th edition 1986.

Combinations with other pesticidally active substances, fertilizers and/or growth regulators can also be prepared on the basis of these formulations, for example in the form of a finished formulation or as a tank mix. Wettable powders are preparations which are uniformly dispersible in water and which, in addition to the active compound and as well as a diluent or inert substance, also contain wetting agents, for example polyoxyethylated alkylphenols, polyoxyethylated fatty alcohols and alkylor alkylphenol-sulfonates, and dispersing agents, for example sodium ligninsulfonate, sodium 2,2'-dinaphthylmethane-6,6'-disulfonate, sodium dibutylnaphthalenesulfonate or sodium oleyl-methyl-taurate. Emulsifiable concentrates are prepared by dissolving the active compound in an organic solvent, for example butanol, cyclohexanone, dimethylformamide, xylene or higher-boiling aromatics or hydrocarbons, with the addition of one or more emulsifiers. Examples of emulsifiers which can be used are: calcium alkylarylsulfonates, such as Ca dodecylbenzenesulfonate, or non-ionic emulsifiers, such as fatty acid polyglycol esters, alkylaryl polyglycol ethers, fatty alcohol polyglycol ethers, propylene oxide/ethylene oxide condensation products, alkyl polyethers, sorbitan fatty acid esters, polyoxyethylene sorbitan fatty acid esters or polyoxyethylene sorbitol esters.

Dusting agents are obtained by grinding the active compound with finely divided solid substances, for example talc or natural clays, such as kaolin, bentonite, pyrophillite or diatomaceous earth. Granules can be prepared either by spraying the active compound onto an adsorbent granular inert material or by applying active compound concentrates to the surface of carrier substances, such as sand, kaolinites or a granular inert material, by means of adhesives, for example polyvinyl alcohol, sodium polyacrylate or alternatively mineral oils. Suitable active compounds can also be granulated in the manner customary for the preparation of fertilizer granules—if desired as a mixture with fertilizers.

The active compound concentration in wettable powders is, for example, about 10 to 90% by weight, the remainder to make up to 100% by weight consisting of customary formulation constituents. The active compound concentration in emulsifiable concentrates can be about 5 to 80% by weight. Dust-like formulations usually contain 5 to 20% by weight of active compound, and sprayable solutions contain about 2 to 20% by weight. The active compound content of granules depends partly on whether the active compound is in liquid or solid form and on what granulation auxiliaries, fillers and the like are used.

The active compound formulations mentioned in addition optionally contain the particular customary tackifiers, wetting agents, dispersing agents, emulsifiers, penetration agents, solvents, fillers or carrier substances.

For use, the concentrates in the commercially available form are diluted in the customary manner, if appropriate, for example by means of water in the case of wettable powders, emulsifiable concentrates, dispersions and in some cases also microgranules. Dust-like and granular formulations and also sprayable solutions are usually not diluted further with extra inert substances before use.

The application amount required varies according to the external conditions, such as temperature, humidity and the like. It can vary within wide limits, for example between 0.005 and 10.0 kg/ha or more of active substance, but is preferably between 0.01 and 5 kg/ha.

The active compounds according to the invention can be present in their commercially available formulations and in the use forms prepared from these formulations as mixtures with other active compounds, such as insecticides, attractants, sterilizing agents, acaricides, nematicides, fungicides, growth-regulating substances or herbicides.

The agents for combating pests include, for example, phosphoric acid esters, carbamates, carboxylic acid esters, formamidines, tin compounds, substances produced by microorganisms and the like.

Preferred mixing partners are 1. from the group of phosphorus compounds acephate, azamethiphos, azinphos-ethyl, azinphos-methyl, bromophos, bromophos-ethyl, chlorfenvinphos, chlormephos, chlorpyrifos, chlorpyrifos-methyl, demeton, demeton-S-methyl, demeton S-methyl sulfone, dialifos, diazinon, dichlorvos, dicrotophos, O,O-1,2,2,2-tetrachloroethylphosphorothioate (SD 208 304), dimethoate, disulfoton, EPN, ethion, ethoprophos, etrimfos, famphur, fenamiphos, fenitriothion, fensulfothion, fenthion, fonofos, formothion, heptenophos, isozophos, isothioate, isoxathion, malathion, methacrifos, methamidophos, methidation, salithion, mevinphos, monocrotophos, naled, omethoate, oxydemeton-methyl, parathion, parathion-methyl, phenthoate, phorate, phosalone, phosfolan, phosmet, phosphamidon, phoxim, pirimiphos-ethyl, pirimiphos-methyl, profenofos, propaphos, proetamphos, prothiofos, pyraclofos, pyridapenthion, quinalphos, sulprofos, temephos, terbufos, tetrachlorvinphos, thiometon, triazophos, trichlorphon and vamidothion;

2. from the group of carbamates aldicarb, 2-sec-butylphenyl methylcarbamate (BPMC), carbaryl, carbofuran, carbosufan, cloethocarb, benfuracarb, ethiofencarb, furathiocarb, isoprocarb, methomyl, 5-methyl-m-cumenylbutyryl (methyl)carbamate, oxamyl, pirimicarb, propoxur, thiodicarb, thiofanox, ethyl 4,6,9-triaza-4-benzyl-6,10-dimethyl-8-oxa-7-oxo-5,11-dithia-9-dodecenoate thia-9-dodecenoate (OK 135) and 1-methylthio(ethylideneamino) N-methyl-N-(morpholinothio)carbamate (UC 51717);

3. from the group of carboxylic acid esters allethrin, alphametrin, 5-benzyl-3-furylmethyl (E)-(1R)-cis-2,2-dimethyl-3-(2-oxothiolan-3-ylidenemethyl)cyclopropanecarboxylate, bioallethrin, bioallethrin((S)-cyclopentyl isomer), bioresmethrin, biphenate, (RS)-1-cyano-1-(6-phenoxy-2-pyridyl)methyl (1RS)-trans-3-(4-tertbutylphenyl)-2,2-dimethylcyclopropanecarboxylate (NCI 85193), cycloprothrin, cyfluthrin, cyhalothrin, cypermethrin, cyphenothrin, deltamethrin, empenthrin, esfenvalerate, fenfluthrin, fenpropathrin, fenvalerate, flucythrinate, flumethrin, fluvalinate (D-isomer), permethrin, pheothrin ((R)-isomer), d-pralethrin, pyrethrins (natural products), resmethrin, tefluthrin, tetramethrin and tralomethrin;

4. from the group of amidines amitraz and chlordimeform;

5. from the group of tin compounds cyhexatin and fenbutatin oxide;

6. others abamectin, Bacillus thuringiensis, bensultap, binapacryl, bromopropylate, buprofezin, camphechlor, cartap, chlorobenzilate, chlorfluazuron, 2-(4-(chlorophenyl)-4,5-diphenylthiophen (UBI-T 930), chlorfentezine, 2-naphthylmethylcyclopropanecarboxylate (Ro 12-0470), cyromazin, ethyl N-(3,5-dichloro-4-

(1,1,2,3,3,3-hexafluoro-1-propyl-oxy)phenyl)carbamoyl)-2-chlorobenzocarboximidate, DDT, dicofol, N-(N-(3,5-dichloro-4-(1,1,2,2-tetrafluoroethoxy)-phenylamino)carbonyl)-2,6-difluorobenzamide (XRD 473), diflubenzuron, N-(2,3-dihydro-3-methyl-1,3-thiazol-2-ylidene)-2,4-xylidene, dinobuton, dinocap, endosulfan, ethofenprox, (4-ethoxyphenyl)(dimethyl)(3-(3-phenoxyphenyl)propyl)silane, (4-ethoxyphenyl)(3-(4-fluoro-3-phenoxyphenyl)propyl)dimethylsilane, fenoxycarb, 2-fluoro-5-(4-(4-ethoxyphenyl)-4-methyl-1-pentyl)diphenyl ether (MTI 800), trachoma and nuclear polyhedrosis viruses, fenthiocarb, flubenzimine, flucycloxuron, flufenoxuron, gamma-HCH, hexythiazox, hydramethylnon (AC 217300), ivermectin, 2-nitromethyl-4,5-dihydro-6H-thiazine (SD 52618), 2-nitromethyl-3,4-dihydrothiazole (SD 35651), 2-nitromethylene-1,2-thiazinan-3-ylcarbamaldehyde (WL 108477), propargite, teflubenzuron, tetradifon, tetrasul, thiocyclam and triflumuron.

The active compound content of the use forms prepared from the commercially available formulations can be from 0.00000001 to 100% by weight of active compound, preferably between 0.00001 and 1% by weight.

The formulations are used in a customary manner suitable for the use forms.

The active compounds according to the invention are also suitable for combating endo- and ectoparasites in the field of veterinary medicine and in the field of animal husbandry.

The active compounds according to the invention are used here in a known manner, such as by oral use in the form of, for example, tablets, capsules, drinks or granules, by dermal use in the form of, for example, dipping, spraying, pouring on and spotting on, and powdering, and by parenteral use in the form of, for example, injection.

The novel compounds of the formula I according to the invention can accordingly also be particularly advantageously used in animal husbandry (for example cattle, sheep, pigs and poultry, such as chickens, geese and the like). In a preferred embodiment of the invention, the novel compounds are administered orally to the animals, if appropriate in suitable formulations (cf. above) and if appropriate with the drinking water or feed. Since excretion in the feces is effective, the development of insects in the feces of the animals can be prevented very simply in this manner. The particular dosages and formulations suitable depend, in particular, on the species and stage of development of the stock animals and also on the threat of attack and can easily be determined and specified by customary methods. The novel compounds can be used on cattle, for example, in dosages of 0.01 to 1 mg/kg of body weight.

The following examples serve to illustrate the invention.

A. FORMULATION EXAMPLES (a) A dusting agent is obtained by mixing 10 parts by weight of active compound and 90 parts by weight of talc, as the inert substance, and comminuting the mixture in an impact mill.

(b) A wettable powder which is readily dispersible in water is obtained by mixing 25 parts by weight of active compound, 65 parts by weight of kaolin-containing quartz, as the inert substance, 10 parts by weight of potassium ligninsulfonate and 1 part by weight of sodium oleoyl-methyl-taurate, as the wetting and dispersing agent, and grinding the mixture in a pinned disk mill.

(c) A dispersion concentrate which is readily dispersible in water is prepared by mixing 40 parts by weight of active compound with 7 parts by weight of a sulfosuccinic acid half-ester, 2 parts by weight of a sodium ligninsulfonate and 51 parts by weight of water and grinding the mixture to a fineness of less than 5 microns in a ball mill.

(d) An emulsifiable concentrate can be prepared from 15 parts by weight of active compound, 75 parts by weight of cyclohexanone, as the solvent, and 10 parts by weight of oxyethylated nonylphenol (10 moles of ethylene oxide), as the emulsifier.

(e) Granules can be prepared from 2 to 15 parts by weight of active compound and an inert granule carrier material, such as attapulgite, pumice granules and/or quartz sand. A suspension of the wettable powder from Example (b) with a solids content of 30% is advantageously used, and this is sprayed onto the surface of attapulgite granules and the granules are dried and mixed intimately. The weight content of the wettable powder here is about 5% and that of the inert carrier material is about 95% of the finished granules.

B. CHEMICAL EXAMPLES (a) Precursors 4-(2-Chloro-4-trifluoromethyl-1-phenylmercapto)aniline 19.86 g (0.1 mole) of 3-chloro-4-fluorobenzotrifluoride and 20 g of anhydrous potassium carbonate were taken in ml of absolute acetonitrile and 12.52 g (0.1 mole) of 4-mercaptoaniline were added dropwise at room temperature. The mixture was stirred at 40° C. for 6 hours, the potassium carbonate was then filtered off and the solvent was distilled off in vacuo. The residue was then taken up in 50 ml of diethyl ether and washed neutral, and after the solvent had been distilled off the residue was recrystallized from cyclohexane.

Yield: 25.2 g (83%)

Melting point: 59°–60° C.

The following was prepared analogously:

4-(2-chloro-4-trifluoromethyl-1-phenylmercapto)-2-fluoroaniline

Melting point: 48° C.

4-(2-Chloro-4-trifluoromethyl-1-phenylmercapto)-phenyl isocyanate 15.19 g (50 mmol) of 4-(2-chloro-4-trifluoromethyl-1-phenylmercapto)aniline and 25 g (0.25 mole) of phosgene in 100 ml of absolute toluene were slowly heated from 0° C. to the reflux temperature, the excess phosgene was driven off with an inert gas and the solvent was evaporated. The oil thus obtained was used for subsequent reactions without further purification.

Yield: 15.7 g (95%)

(b) End products

EXAMPLE 1

N-(2-Chlorobenzoyl)-N'-(4-(2-chloro-4-trifluoromethyl-1-phenylmercapto)phenyl)urea 1.56 g (10 mmol) of 2-chlorobenzamide and 3.30 g (10 mmol) of 4-(2-chloro-4-trifluoromethyl-1-phenylmercapto)phenyl isocyanate were boiled under reflux in 10 ml of absolute toluene for 3 hours. After cooling, the crystals which had precipitated were filtered off with suction, washed with toluene and dried.

Yield: 4.46 g (92%)

Melting point: 186° C.

EXAMPLE 2

N-(4-(2-Chloro-4-trifluoromethyl-1-phenylmercapto)-phenyl)-N'-(2,6-difluorobenzoyl)urea 3.03 g (10 mmol) of 4-(2-chloro-4-trifluoromethyl-1-phenylmercapto)aniline were taken in 5 ml of absolute n-heptane, 1.83 g (10 mmol) of 2,6-difluorobenzoyl isocyanate were added dropwise and the mixture was subsequently stirred at room temperature for 2 hours. The crystals were filtered off with suction and recrystallized from toluene.

Yield: 4.33 g (89%)

Melting point: 197° C.

The compounds of the formula I listed in the following table can be prepared in an analogous manner.

TABLE 1

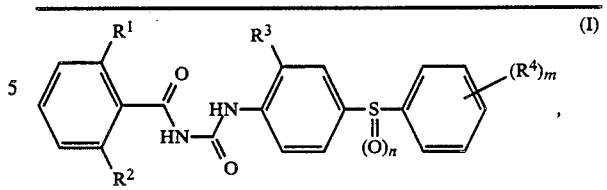

| Ex. No. | $R^1$ | $R^2$ | $R^3$ | $(R^4)_m$ | n | Fp (°C.) |
|---|---|---|---|---|---|---|
| 3 | F | H | H | 2-Cl, 4-CF$_3$ | 0 | 178 |
| 4 | Cl | H | H | 2-Cl, 4-CF$_3$ | 1 | 220 |
| 5 | F | H | H | 2-Cl, 4-CF$_3$ | 1 | |
| 6 | F | F | H | 2-Cl, 4-CF$_3$ | 1 | |
| 7 | Cl | H | H | 2-Cl, 4-CF$_3$ | 2 | |
| 8 | F | H | H | 2-Cl, 4-CF$_3$ | 2 | |
| 9 | F | F | H | 2-Cl, 4-CF$_3$ | 2 | |
| 10 | Cl | H | F | 2-Cl, 4-CF$_3$ | 0 | 162 |
| 11 | F | H | F | 2-Cl, 4-CF$_3$ | 0 | |
| 12 | F | F | F | 2-Cl, 4-CF$_3$ | 0 | 177 |
| 13 | Cl | H | Cl | 2-Cl, 4-CF$_3$ | 0 | 104 |
| 14 | F | H | Cl | 2-Cl, 4-CF$_3$ | 0 | |
| 15 | F | F | Cl | 2-Cl, 4-CF$_3$ | 0 | 106 |
| 16 | Cl | H | H | 2-F, 4-CF$_3$ | 0 | 151–152 |
| 17 | F | H | H | 2-F, 4-CF$_3$ | 0 | 171–172 |
| 18 | F | F | H | 2-F, 4-CF$_3$ | 0 | 190–191 |
| 19 | Cl | H | F | 2-F, 4-CF$_3$ | 0 | |
| 20 | F | H | F | 2-F, 4-CF$_3$ | 0 | |
| 21 | F | F | F | 2-F, 4-CF$_3$ | 0 | |
| 22 | Cl | H | H | 2-CF$_3$, 4-Cl | 0 | |
| 23 | F | H | H | 2-CF$_3$, 4-Cl | 0 | |
| 24 | F | F | H | 2-CF$_3$, 4-Cl | 0 | 158 |
| 25 | Cl | H | H | 3-Cl, 4-CF$_3$ | 0 | 148 |
| 26 | F | H | H | 3-Cl, 4-CF$_3$ | 0 | |
| 27 | F | F | H | 3-Cl, 4-CF$_3$ | 0 | 175 |
| 28 | Cl | H | H | 2-CF$_3$, 5-Cl | 0 | |
| 29 | F | H | H | 2-CF$_3$, 5-Cl | 0 | |
| 30 | F | F | H | 2-CF$_3$, 5-Cl | 0 | |
| 31 | Cl | H | H | 2,6-Cl$_2$, 4-CF$_3$ | 0 | 179–180 |
| 32 | F | H | H | 2,6-Cl$_2$, 4-CF$_3$ | 0 | 186–187 |
| 33 | F | F | H | 2,6-Cl$_2$, 4-CF$_3$ | 0 | 185–186 |
| 34 | Cl | H | F | 2,6-Cl$_2$, 4-CF$_3$ | 0 | |
| 35 | F | H | F | 2,6-Cl$_2$, 4-CF$_3$ | 0 | |
| 36 | F | F | F | 2,6-Cl$_2$, 4-CF$_3$ | 0 | |
| 37 | Cl | H | H | 2-NO$_2$, 4-CF$_3$ | 0 | 235–238 |
| 38 | F | H | H | 2-NO$_2$, 4-CF$_3$ | 0 | 200–202 |
| 39 | F | F | H | 2-NO$_2$, 4-CF$_3$ | 0 | 226 |
| 40 | Cl | H | H | 3-CF$_3$, 4-NO$_2$ | 0 | 168–170 |
| 41 | F | H | H | 3-CF$_3$, 4-NO$_2$ | 0 | 189 |
| 42 | F | F | H | 3-CF$_3$, 4-NO$_2$ | 0 | 205–206 |
| 43 | Cl | H | H | 2-Cl, 4-NO$_2$ | 0 | 226–227 |
| 44 | F | H | H | 2-Cl, 4-NO$_2$ | 0 | 208–209 |
| 45 | F | F | H | 2-Cl, 4-NO$_2$ | 0 | 217–218 |
| 46 | F | H | H | 2,6-(NO$_2$)$_2$, 4-CF$_3$ | 0 | |
| 47 | F | F | H | 2,6-(NO$_2$)$_2$, 4-CF$_3$ | 0 | 236–238 |
| 48 | Cl | H | H | 2,4-(NO$_2$)$_2$, 6-CF$_3$ | 0 | 216–219 |
| 49 | F | H | H | 2,4-(NO$_2$)$_2$, 6-CF$_3$ | 0 | |
| 49a | Cl | H | H | 2,6-(NO$_2$)$_2$, 4-CF$_3$ | 0 | 232–233 |
| 50 | F | F | H | 2,4-(NO$_2$)$_2$, 6-CF$_3$ | 0 | 216–217 |
| 51 | Cl | H | H | 2,6-(NO$_2$)$_2$, 3-Cl, 4-CF$_3$ | 0 | |
| 52 | F | H | H | 2,6-(NO$_2$)$_2$, 3-Cl, 4-CF$_3$ | 0 | |
| 52a | F | F | H | 2,6-(NO$_2$)$_2$, 3-Cl, 4-CF$_3$ | 0 | |
| 52b | Cl | H | H | 2-CF$_3$, 4-NO$_2$ | 0 | 224–226 |
| 52c | F | H | H | 2-CF$_3$, 4-NO$_2$ | 0 | 236 |
| 52d | F | F | H | 2-CF$_3$, 4-NO$_2$ | 0 | 249 |
| 52e | Cl | H | H | 3-Cl, 4-CF$_3$, 5-NO$_2$ | 0 | 242–245 |
| 52f | F | H | H | 3-Cl, 4-CF$_3$, 5-NO$_2$ | 0 | 248–250 |
| 52g | Cl | H | F | 2-Cl, 4-CF$_3$ | 2 | 165 |
| 52h | F | F | H | 4-CF$_3$ | 0 | 194 |
| 52i | Cl | H | H | 4-CF$_3$ | 0 | 173 |
| 52j | Cl | H | H | 2-Br, 4-CF$_3$ | 0 | 157 |
| 52k | Br | H | F | 2-Cl, 4-CF$_3$ | 0 | 160 |
| 52l | F | Cl | F | 2-Cl, 4-CF$_3$ | 0 | 158 |
| 52m | Cl | H | F | 2-CF$_3$, 4-NO$_2$ | 0 | 214 |
| 52n | Cl | H | H | 2-NO$_2$, 4-CF$_3$ | 0 | 238 |
| 52o | Cl | H | F | 2-Cl, 4-NO$_2$ | 0 | 197 |
| 52p | Cl | H | Br | 2-Cl, 4-CF$_3$ | 0 | 97 |
| 52q | Cl | H | F | 3-CF$_3$ | 0 | 147 |

EXAMPLE 53

2-(2-Chlorophenyl)5-(4-(2-chloro-4-trifluoromethyl-1-phenylmercapto)phenyl)-6H-1,3,5-oxadiazine-4,6-dione 1.81 g (10 mmol) of 2-chlorobenzoyl isocyanate and 3.30 g (10 mmol) of 4-(2-chloro-4-trifluoromethylphenylmercapto)phenyl isocyanate were stirred at 70° C. for 16 hours, with exclusion of moisture. After cooling, the mixture was stirred with 5 ml of absolute n-heptane and the solid was filtered off with suction and recrystallized from toluene.

Yield: 4.34 g (85%)

Melting point: 193°–194° C.

The following compounds of the formula I can be prepared by a procedure analogous to that described in Example 53 (Table 2):

TABLE 2

| Ex. No. | $R^1$ | $R^2$ | $R^3$ | $(R^4)_m$ | n | Fp (°C.) |
|---|---|---|---|---|---|---|
| 54 | F | H | H | 2-Cl, 4-CF$_3$ | 0 | 183–184 |
| 55 | F | F | H | 2-Cl, 4-CF$_3$ | 0 | 174–175 |
| 56 | Cl | H | H | 2-Cl, 4-CF$_3$ | 1 | |
| 57 | F | H | H | 2-Cl, 4-CF$_3$ | 1 | |
| 58 | F | F | H | 2-Cl, 4-CF$_3$ | 1 | |
| 59 | Cl | H | H | 2-Cl, 4-CF$_3$ | 2 | |
| 60 | F | H | H | 2-Cl, 4-CF$_3$ | 2 | |
| 61 | F | F | H | 2-Cl, 4-CF$_3$ | 2 | |
| 62 | Cl | H | F | 2-Cl, 4-CF$_3$ | 0 | |

TABLE 2-continued

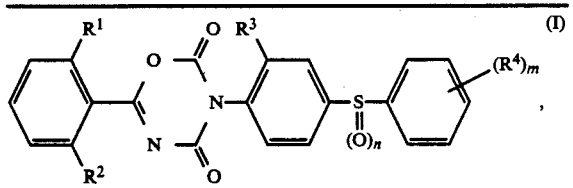

(I)

| Ex. No. | R¹ | R² | R³ | (R⁴)m | n | Fp (°C.) |
|---|---|---|---|---|---|---|
| 63 | F | H | F | 2-Cl, 4-CF₃ | 0 | |
| 64 | F | F | F | 2-Cl, 4-CF₃ | 0 | |
| 65 | Cl | H | Cl | 2-Cl, 4-CF₃ | 0 | |
| 66 | F | H | Cl | 2-Cl, 4-CF₃ | 0 | |
| 67 | F | F | Cl | 2-Cl, 4-CF₃ | 0 | |
| 68 | Cl | H | H | 2-F, 4-CF₃ | 0 | |
| 69 | F | H | H | 2-F, 4-CF₃ | 0 | |
| 70 | F | F | H | 2-F, 4-CF₃ | 0 | |
| 71 | Cl | H | F | 2-F, 4-CF₃ | 0 | |
| 72 | F | H | F | 2-F, 4-CF₃ | 0 | |
| 73 | F | F | F | 2-F, 4-CF₃ | 0 | |
| 74 | Cl | H | H | 2-CF₃, 4-Cl | 0 | |
| 75 | F | H | H | 2-CF₃, 4-Cl | 0 | |
| 76 | F | F | H | 2-CF₃, 4-Cl | 0 | |
| 77 | Cl | H | H | 3-Cl, 4-CF₃ | 0 | |
| 78 | Cl | H | H | 2,6-Cl₂, 4-CF₃ | 0 | |
| 79 | F | H | H | 2,6-Cl₂, 4-CF₃ | 0 | |
| 80 | F | F | H | 2,6-Cl₂, 4-CF₃ | 0 | |
| 81 | Cl | H | F | 2,6-Cl₂, 4-CF₃ | 0 | |
| 82 | F | H | F | 2,6-Cl₂, 4-CF₃ | 0 | |

EXAMPLE 83

Ethyl N-(N-(4-(2-chloro-4-trifluoromethyl-1-phenylmercapto)phenyl)carbamoyl)-2-chlorobenzocarboximidate 1.83 g (10 mmol) of ethyl 2-chlorobenzocarboximidate were cooled to 0° C. and 3.30 g (10 mmol) of 4-(2-chloro-4-trifluoromethylphenylmercapto)phenyl isocyanate were added dropwise, while stirring. After 3 hours, 5 ml of absolute n-heptane were added, the mixture was stirred and the solid was filtered off with suction.

Yield: 4.67 g (91%)

Melting point: 94°–85° C.

The following compounds of Table 3 can be prepared by a procedure analogous to that described in Example 83:

TABLE 3

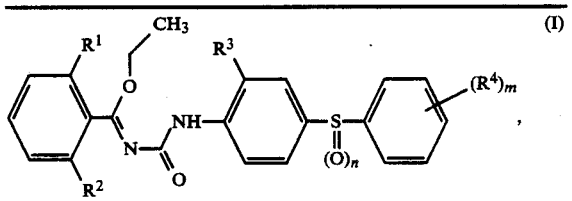

(I)

| Ex. No. | R¹ | R² | R³ | (R⁴)m | n | Fp (°C.) |
|---|---|---|---|---|---|---|
| 84 | F | H | H | 2-Cl, 4-CF₃ | 0 | 79–80 |
| 85 | F | F | H | 2-Cl, 4-CF₃ | 0 | 103–104 |
| 86 | Cl | H | H | 2-Cl, 4-CF₃ | 1 | |
| 87 | F | H | H | 2-Cl, 4-CF₃ | 1 | |
| 88 | F | F | H | 2-Cl, 4-CF₃ | 1 | |
| 89 | Cl | H | H | 2-Cl, 4-CF₃ | 2 | |
| 90 | F | H | H | 2-Cl, 4-CF₃ | 2 | |
| 91 | F | F | H | 2-Cl, 4-CF₃ | 2 | |
| 92 | Cl | H | F | 2-Cl, 4-CF₃ | 0 | |
| 93 | F | H | F | 2-Cl, 4-CF₃ | 0 | |
| 94 | F | F | F | 2-Cl, 4-CF₃ | 0 | |
| 95 | Cl | H | Cl | 2-Cl, 4-CF₃ | 0 | |
| 96 | F | H | Cl | 2-Cl, 4-CF₃ | 0 | |
| 97 | F | F | Cl | 2-Cl, 4-CF₃ | 0 | |

TABLE 3-continued

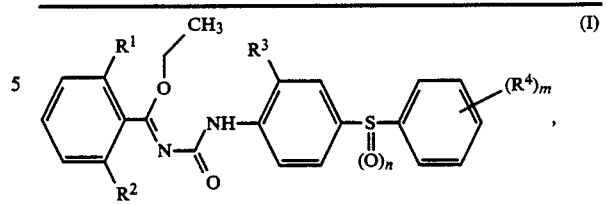

(I)

| Ex. No. | R¹ | R² | R³ | (R⁴)m | n | Fp (°C.) |
|---|---|---|---|---|---|---|
| 98 | Cl | H | H | 2-F, 4-CF₃ | 0 | 87–88 |
| 99 | F | H | H | 2-F, 4-CF₃ | 0 | 79–80 |
| 100 | F | F | H | 2-F, 4-CF₃ | 0 | 94–95 |
| 101 | Cl | H | F | 2-F, 4-CF₃ | 0 | |
| 102 | F | H | F | 2-F, 4-CF₃ | 0 | |
| 103 | F | F | F | 2-F, 4-CF₃ | 0 | |
| 104 | Cl | H | H | 2-CF₃, 4-Cl | 0 | |
| 105 | F | H | H | 2-CF₃, 4-Cl | 0 | |
| 106 | F | F | H | 2-CF₃, 4-Cl | 0 | |
| 107 | Cl | H | H | 3-Cl, 4-CF₃ | 0 | |
| 108 | F | H | H | 3-Cl, 4-CF₃ | 0 | |
| 109 | F | F | H | 3-Cl, 4-CF₃ | 0 | |
| 110 | Cl | H | H | 2-CF₃, 5-Cl | 0 | |
| 111 | F | H | H | 2-CF₃, 5-Cl | 0 | |
| 112 | F | F | H | 2-CF₃, 5-Cl | 0 | |
| 113 | Cl | H | H | 2,6-Cl₂, 4-CF₃ | 0 | |
| 114 | F | H | H | 2,6-Cl₂, 4-CF₃ | 0 | |
| 115 | F | F | H | 2,6-Cl₂, 4-CF₃ | 0 | |
| 116 | Cl | H | F | 2,6-Cl₂, 4-CF₃ | 0 | |
| 117 | F | H | F | 2,6-Cl₂, 4-CF₃ | 0 | |
| 118 | F | F | F | 2,6-Cl₂, 4-CF₃ | 0 | |
| 119 | Cl | H | H | 2-NO₂, 4-CF₃ | 0 | |
| 120 | F | H | H | 2-NO₂, 4-CF₃ | 0 | |
| 121 | F | F | H | 2-NO₂, 4-CF₃ | 0 | |
| 122 | Cl | H | H | 3-CF₃, 4-NO₂ | 0 | |
| 123 | F | H | H | 3-CF₃, 4-NO₂ | 0 | |
| 124 | F | F | H | 3-CF₃, 4-NO₂ | 0 | |
| 125 | Cl | H | H | 2-Cl, 4-NO₂ | 0 | 132–133 |
| 126 | F | H | H | 2-Cl, 4-NO₂ | 0 | 127–128 |
| 127 | F | F | H | 2-Cl, 4-NO₂ | 0 | 119–120 |
| 128 | Cl | H | H | 2,6-(NO₂)₂, 4-CF₃ | 0 | |
| 129 | F | H | H | 2,6-(NO₂)₂, 4-CF₃ | 0 | |
| 130 | F | F | H | 2,6-(NO₂)₂, 4-CF₃ | 0 | |
| 131 | Cl | H | H | 2,4-(NO₂)₂, 6-CF₃ | 0 | |
| 132 | F | H | H | 2,4-(NO₂)₂, 6-CF₃ | 0 | |
| 133 | F | F | H | 2,4-(NO₂)₂, 6-CF₃ | 0 | |
| 134 | Cl | H | H | 2,6-(NO₂)₂, 3-Cl, 4-CF₃ | 0 | |
| 135 | F | F | H | 2,6-(NO₂)₂, 3-Cl, 4-CF₃ | 0 | |

TABLE 4

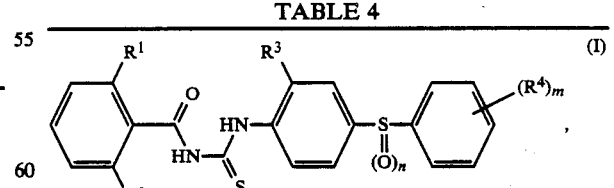

(I)

| Ex. No. | R¹ | R² | R³ | (R⁴)m | n | Fp (°C.) |
|---|---|---|---|---|---|---|
| 136 | Cl | H | H | 2-Cl, 4-CF₃ | 0 | 125–126 |
| 137 | F | H | H | 2-Cl, 4-CF₃ | 0 | 103–105 |
| 138 | Cl | H | F | 2-Cl, 4-CF₃ | 0 | 125 |
| 139 | F | F | F | 2-Cl, 4-CF₃ | 0 | 148 |

C. BIOLOGICAL EXAMPLES

EXAMPLE 1

(Spodoptera Test)

Larvae of the African cottonworm (Spodoptera littoralis L III) and Petri dishes filled with an agar-based diet were sprayed in a spraying apparatus with an active compound formulation having a concentration of 100 ppm. After the spray coating had dried, the larvae were placed on the treated agar diet. After the desired period (7 days, moulting to L IV), the destruction of the caterpillars in % was determined. 100% here means that all the caterpillars were destroyed.

100% mortality was to be found with the compounds of Examples 1, 2, 3, 10, 12, 15, 16, 17, 18, 24, 31, 33, 37, 38, 39, 40, 42, 43, 45, 48, 50, 55, 83, 84, 85, 52b, 52c, 52d, 52g to 52q and 136–139 in the above concentration.

EXAMPLE 2

(Musca Test)

Housefly larvae (Musca domestica) 24 hours old were introduced into a fly diet into which an active compound formulation had previously been incorporated up to an active compound concentration of 250 ppm. After the desired period (L1 to hatching of the flies), the destruction of the larvae or the hatching of the flies was determined in %. 100% here means that all the larvae had been destroyed or that no flies had hatched from the puppae.

100% action was to be found with the compounds 1, 2, 3, 10, 12, 15, 16, 17, 18, 24, 25, 31, 33, 37, 38, 39, 40, 41, 42, 43, 44, 45, 47, 48, 50, 55, 83, 84, 85, 52b, 52c, 52d, 52e, 52f, 52h, 52i, 52k–52q and 136–139 in the above concentration.

EXAMPLE 3

(Lucitia Test)

The active substances were dissolved in a mixture consisting of dimethylformamide (85 g), $^R$Emulsogen (7 g) and $^R$Arkopal N 60 (3 g) so that dilution series having active compound concentrations of 10,000/1,000/100 ppm are obtained. 1 ml portions of these solutions are mixed intimately with 9 g of finely ground meat, so that meat having active compound concentrations of 1,000/100/10 ppm finally exists. As a control, 1 ml of the solvent are added to 9 g of meat.

20 freshly hatched larvae of Lucilia cuprina are added to each of the larvae nutrient media thus prepared. After 72 hours, when the larvae I have developed to the puppation-ready larvae III in the control medium, the mortality rate is determined. In this test, the compounds according to Example 2, 10, 15, 16, 18, 33, 136 and 138 resulted in 100% destruction of the larvae at an active compound concentration of 10 ppm.

EXAMPLE 4

(Periplaneta Test)

Cockroaches (Periplaneta germanica larvae L III) were placed in Petri dishes in which in each case 1 ml of an aqueous active compound formulation of the compounds mentioned below had been applied on the inside of the base and of the lid. The active compound concentration here was 500 ppm, based on the carrier medium water. Before introduction of the cockroaches, the water was evaporated off, so that the test animals were exposed to the active compound coating which was uniformly on the inside. After 5 days, the dead animals were determined. It was found that a 100% destructive action was caused by the compounds 1, 2, 16, 18, 31, 33, 37, 38, 40, 41, 42, 43, 44, 45, 55, 83, 84, 85, 52b–52f, 52h, 52i, 52k–52q and 136–139 in the above active compound concentration.

EXAMPLE 5

(Trialeurodes Test)

Bean plants heavily infested with white fly (*Trialeurodes vaporariorum*) were sprayed with aqueous suspensions of wettable powder concentrates (active compound content 200 ppm) until the concentrates started to drip off. After the plants had been placed in a greenhouse, a microscopic control was performed, with the result of in each case 100% mortality with the preparations containing the active compounds of Examples 1, 2, 52h, 52j, 52l, 136 and 139.

EXAMPLE 6

(Tetranychus Test)

Bean plants (Phaseolus v.) heavily infested with bean spider mites (*Tetranychus urticae*) were sprayed with the aqueous dilution of an emulsion concentrate containing 100 ppm of the particular active compound. 100% destruction was achieved with the compounds according to Example 1, 2, 10, 12, 15, 16, 18, 24, 25, 33, 37, 38, 39, 43, 55, 83, 84, 85, 52g to 52n, 52p and 136–139.

EXAMPLE 7

(Panonychus Test)

Apple trees heavily infested with fruit tree spider mites (*Panonychus ulmi*) were sprayed with the aqueous dilution of an emulsion concentrate containing 100 ppm of the particular active compound.

100% destruction was achieved with the compounds according to Example 1, 2, 3, 10, 12, 16, 18, 25, 37, 38, 39, 40, 45, 55, 83, 84, 85, 52g–52l, 52p and 136–139.

I claim:

1. A compound of formula I (I)

in which A is the radical A$^1$ (A$^1$)

R$^1$ to R$^3$ in each case independently of one another are hydrogen or halogen, the radicals R$^4$ in each case independently of one another are halogen, (C$_1$–C$_3$) halogenoalkyl or nitro, X is oxygen n is 0 and m is a number from 1 to 4 or, an agriculturally suitable salt thereof, provided that $(R^4)_m$ is not by itself halogen or is not by itself nitro.

2. A compound of formula I as claimed in claim 1, in which $R^1$ is Cl or F and $R^2$ is H or F; $R^3$ is H or F and the radicals $R^4$ in each case independently of one another are Cl, F, $CF_3$ or nitro; m is 1 to 3, and, an agriculturally suitable salt thereof.

3. A compound of formula I as claimed in claim 1, in which $R^1$ is Cl or F and $R^2$ is H or F; $R^3$ is H or F and $(R^4)_m$ is 2-Cl or 4-$CF_3$; m is 1 or 2, and, an agriculturally suitable salt thereof.

4. The compound N-(2-fluorobenzoyl)-N'-(4-(2-chloro-4-trifluoromethyl-1-phenylmercapto)phenyl)urea.

5. The compound N-(2-chlorobenzoyl)-N'-(4-(2-chloro-4-trifluoromethyl-1-phenylmercapto)phenyl)urea.

6. The compound N-(2,6-difluorobenzoyl)-N'-(4-(2-chloro-4-trifluoromethyl-1-phenylmercapto)phenyl)urea.

7. The compound N-(2-chlorobenzoyl)-N'-(4-(2-chloro-4-trifluoromethyl-1-phenylmercapto)-2-fluorophenyl)urea.

8. The compound N-(2-fluorobenzoyl)-N'-(4-(2-chloro-4-trifluoromethyl-1-phenylmercapto)-2-fluorophenyl)urea.

9. The compound N-(2,6-difluorobenzoyl)-N'-(4-(2-chloro-4-trifluoromethyl)-1-phenylmercapto)-2-fluorophenyl)urea.

10. An acaridical or insecticidal agent which comprises an effective amount of a compound of formula I as claimed in claim 1 and a suitable carrier therefor.

11. A method for combating acarides or harmful insects, which comprises applying an effective amount of a compound of formula I as claimed in claim 1 to an acaride or harmful insect or to a plant, area or substrate affected by said acaride or harmful insect.

* * * * *